United States Patent [19]

DeHaven-Hudkins et al.

[11] Patent Number: 5,286,733
[45] Date of Patent: Feb. 15, 1994

[54] SUBSTITUTED 3-PIPERIDINEALKANOATES AND ALKANONES AND COMPOSITIONS AND METHOD OF USE THEREOF

[75] Inventors: Diane L. DeHaven-Hudkins, Chester Springs, Pa.; John P. Mallamo, Kinderhook; William F. Michne, Poestenkill, both of N.Y.; Martha R. Heimann, Durham, N.C.

[73] Assignee: Sterling Winthrop Inc., New York, N.Y.

[21] Appl. No.: 979,028

[22] Filed: Nov. 20, 1992

[51] Int. Cl.$^5$ ............... A61K 31/445; C07D 211/34; C07D 405/12
[52] U.S. Cl. .................... 514/315; 514/259; 514/307; 514/317; 514/326; 546/112; 546/146; 546/147; 546/207; 546/208; 546/209; 546/210; 546/211; 546/212; 546/213; 546/214; 546/237; 546/238; 546/248
[58] Field of Search ............... 546/237, 238, 248, 207, 546/208, 209, 210, 211, 212, 213, 214, 112, 146, 147; 514/315, 317, 326, 299, 307

[56] References Cited

U.S. PATENT DOCUMENTS

| | | | |
|---|---|---|---|
| 3,431,267 | 3/1969 | Welcher | 546/240 |
| 3,962,257 | 6/1976 | Pioch | 546/237 |
| 5,023,266 | 6/1991 | Langer et al. | 514/317 |
| 5,071,859 | 12/1991 | Knudsen | 546/208 |

FOREIGN PATENT DOCUMENTS

| | | |
|---|---|---|
| 449187 | 10/1991 | European Pat. Off. . |
| 445195 | 11/1991 | European Pat. Off. . |

OTHER PUBLICATIONS

Cerrinka "Znamines III" CA 54:13126d (1960).
"Pnamines V" CA 55:4507 c (1961).
Chizhov "Derivative of 1-azabicydo[3.2.1]octane" CA 57:2183g (1962).
Loew, et al., Endog. Exog. Opiate Agonists and Antagonists, E. L. Way, editor, Pergamon: Elmsford, N.Y., 1980, pp. 39–42.
Glennon, et al., J. Med. Chem. 1991, 34, 3360–3365.

*Primary Examiner*—C. Warren Ivy
*Assistant Examiner*—Celia Chang
*Attorney, Agent, or Firm*—Alexander, Michael D.; Paul E. Dupont

[57] ABSTRACT

The invention is related to compounds, being useful in treating psychosis, of the formula:

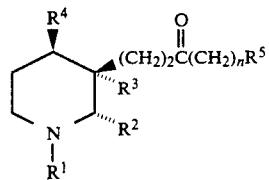

wherein:
$R^1$ is hydrogen, lower-alkyl, phenyl-lower-alkyl, $C_3$–$C_7$-monocyclic cycloalkyl-lower-alkyl, or hydroxy-$C_3$–$C_7$-monocycliccycloalkyl-lower-alkyl;
$R^2$ is lower-alkyl;
$R^3$ is hydrogen or lower-alkyl;
$R^4$ is lower-alkyl;
n is an integer from zero to three; and
$R^5$ is hydroxy, lower-alkoxy, lower-alkyl, $C_3$–$C_7$-monocyclic cycloalkyl, phenyl, or a 5-membered heterocycle selected from furanyl, thienyl and isoxazolyl;
with the proviso that when n is zero, $R^5$ is other than hydroxy or a pharmaceutically acceptable acid-addition salt thereof.

12 Claims, No Drawings

SUBSTITUTED 3-PIPERIDINEALKANOATES AND ALKANONES AND COMPOSITIONS AND METHOD OF USE THEREOF

BACKGROUND OF THE INVENTION (a) Field of the Invention

The invention relates to novel substituted 3-piperidinealkanoates and alkanones, to compositions containing the same, to the method of use thereof in the treatment of central nervous system disorders, and to processes for their preparation.

A number of know antipsychotic drugs are disclosed in the art which have been shown to share a selective, high affinity for sigma receptors, which are sites where psychotomimetic opiates, such as (+)-pentazocine and N-allylnormetazocine, act. It has been suggested that the antipsychotic behavioral profile of these antipsychotic drugs can be attributed to their role as competitive antagonists of sigma receptor binding and that a systematic screen for drugs that block sigma receptors may provide a valuable strategy for identifying novel antipsychotic agents. Additionally, it has been shown that the relative potencies of these agents studied in vivo correspond well with their relative binding affinities obtained in vitro. See, for example, Synder and Largent, J. Neuropsychiatry 1989, 1(1), 7-15; Largent, et al., Eur. J. Pharmacol. 1988, 155, 345-347; Deutsch, et al., Clinical Neuropharmacology 1988, 11(2), 105-119; Tayler, et al., Drug Development Research 1987, 11, 65-70; Ferris, et al., Life Sciences 1986, 38(25), 2329-2337; and Su, et al., Neuroscience Letters 1986, 71, 224-228.

(b) Information Disclosure Statement

Welcher, U.S. Pat. No. 3,431,267, issued Mar. 4, 1969, discloses 2,3-dimethyl-3-piperidinepropanamine

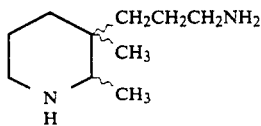

as a fungicide and pesticide.

Loew, et al., Endog. Exog. Opiate Agonists and Antagonists, E. L. Way editor, Pergamon: Elmsford, New York 1980, pp 39-42, disclose 1-$R_1$-2,3,4,4-tetramethyl-piperidines of general formula

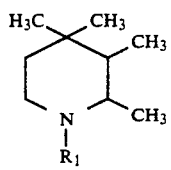

wherein $R_1$ is 3-furanylmethyl, 2-furanylmethyl, 2-propenyl, cyclopropylmethyl, phenylethyl, methyl and hydrogen, without an indication of utility.

Langer, et al., U.S. Pat. No. 5,023,266, issued Jun. 11, 1991, disclose compounds of the formula:

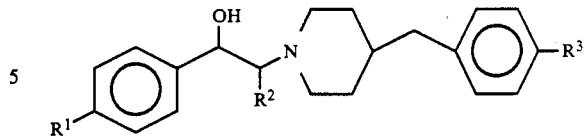

wherein:

$R^1$ denotes a halogen atom or a hydroxy group;
$R^2$ denotes a hydrogen atom or a methyl group; and
$R^3$ denotes a hydrogen or halogen atom.
The compounds are said to be useful in the treatment of psychotic disorders.

Gray and Cheng, European Patent Application 445195, published Nov. 6, 1991, disclose a series of ethanobicyclic amine derivatives which are said to be useful in the treatment of CNS disorders such as psychotic disorders, convulsions, dystonia and cerebral ischemia.

Cain, et al., European Patent Application 449187, published Oct. 2, 1991, disclose a series of disubstituted piperidine ether derivatives which are said to be useful in treating physiological or drug induced psychosis or dyskinesia in mammals or fungal disease in plants.

Glennon, et al., J. Med. Chem. 1991, 34, 3360-3365, disclose a series of novel 4-phenylpiperidine derivatives which are stated to bind with high affinity to sigma receptors.

SUMMARY OF THE INVENTION

The invention relates to a compound of Formula I:

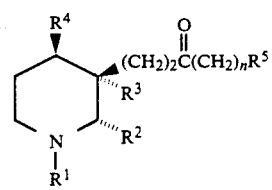

wherein:
$R^1$ is hydrogen, lower-alkyl, phenyl-lower-alkyl, cycloalkyl-lower-alkyl, or hydroxycycloalkyl-lower-alkyl;
$R^2$ is lower-alkyl;
$R^3$ is hydrogen or lower-alkyl;
$R^4$ is lower-alkyl; or $R^3$ and $R^4$ together are —$(CH_2)_m$ wherein m is an integer from three to five;
n is an integer from zero to three; and
$R^5$ is hydroxy, lower-alkoxy, lower-alkyl, cycloalkyl, phenyl, or a 5-membered aromatic monocyclic heterocycle containing from 1 to 2 heteroatoms selected from the group consisting of oxygen, nitrogen and sulfur;
or a pharmaceutically acceptable acid-addition salt thereof.

The compounds of the present invention bind with high affinity to sigma receptors and are thus useful in the treatment of central nervous system disorders.

Preferred compounds of Formula I above are those wherein:
$R^1$ is hydrogen, lower-alkyl, phenyl-lower-alkyl or hydroxycycloalkyl-lower-alkyl;
$R^2$ is lower-alkyl;
$R^3$ is lower-alkyl;
$R^4$ is lower-alkyl; or $R^3$ and $R^4$ together are —$(CH_2)_4$;
n is an integer from zero to three; and $R^5$ is lower-alkoxy, cycloalkyl or a 5-membered aromatic monocyclic heterocycle containing 1 heteroatom selected from the group consisting of oxygen, and sulfur.

Particularly preferred compounds of Formula I above are those wherein:

$R^1$ is hydrogen, methyl, benzyl or hydroxycyclopropylmethyl;

$R^2$ is methyl;

$R^3$ and $R^4$ are methyl; or $R^3$ and $R^4$ together are —$(CH_2)_4$;

n is zero or two; and $R^5$ is lower-alkoxy, cycloalkyl, or furanyl.

The invention further relates to pharmaceutical compositions which comprise a compound of Formula I together with a pharmaceutically acceptable carrier, adjuvant, diluent or vehicle.

The invention further relates to a method for the treatment of central nervous system disorders, especially psychoses, which comprises administering to a patient in need of such treatment an effective amount of a compound of Formula I.

The invention further relates to a process for preparing a compound of Formula I which comprises reacting a compound of Formula II:

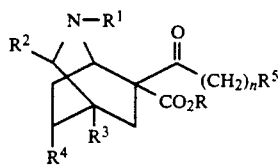

with formic acid in the presence of a base.

DETAILED DESCRIPTION INCLUSIVE OF PREFERRED EMBODIMENTS

The term lower-alkyl as used herein means linear or branched hydrocarbon chains having one to about four carbon atoms and thus includes methyl, ethyl, propyl, isopropyl, n-butyl, sec-butyl, and the like.

The term lower-alkoxy as used herein means linear or branched alkyloxy substituents having one to about four carbon atoms and thus includes methoxy, ethoxy, propoxy, isopropoxy, butoxy, sec-butoxy, and the like.

The term cycloalkyl as used herein means monocyclic hydrocarbon ring systems having three to about seven carbon atoms and thus includes cyclopropyl, cyclobutyl, cyclopentyl, cyclohexyl and cycloheptyl.

The term hydroxycycloalkyl as used herein means cycloalkyl as defined above, substituted by a hydroxy group, and thus includes hydroxycyclopropyl, hydroxycyclobutyl, hydroxycyclopentyl, hydroxycyclohexyl and hydroxycycloheptyl.

The term halogen, halo or halide as used herein means bromine, chlorine, iodine, or fluorine.

The synthesis of compounds of the invention may be outlined as shown in Scheme A:

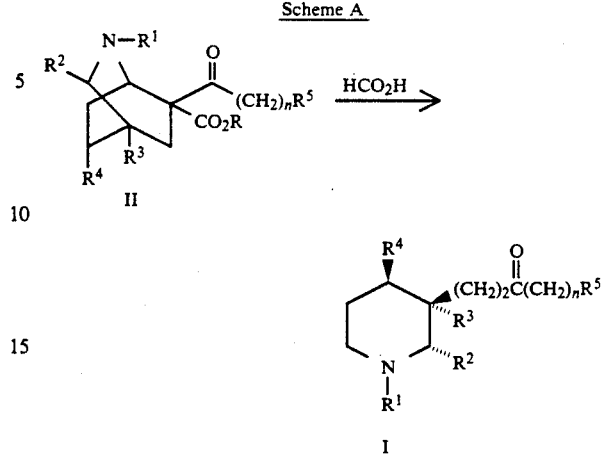

A suitably substituted lower-alkyl 6-acyl-2-azabicyclo[2.2.2]octane-6-carboxylate (II, R=lower-alkyl, preferably ethyl, $R^1$ is other than hydroxycycloalkyl-lower-alkyl), is treated with an excess of formic acid, and an excess of a base, preferably triethylamine, in the absence of a solvent, at a temperature in the range from about 110° C. up to about 160° C. Alternatively, the reaction can be carried out by the treatment of a lower-alkyl 6-acyl-2-azabicyclo[2.2.2]octane-6-carboxylate of Formula II with an excess of formic acid, in a solvent, preferably mesitylene, at a temperature in the range of from about 140° C. up to the boiling point of the solvent used. It will be noted, however, that the compounds of Formula II wherein $R^5$ is lower-alkoxy when n is zero do not undergo this latter reaction.

In those instances when it is desirable to prepare compounds of Formula I wherein $R^1$ is other than benzyl, and in particular when compounds of the Formula I wherein $R^1$ is a substituent which may not survive the above-identified reaction conditions, for example, a hydroxycycloalkyl-lower-alkyl group, are desired, it is preferred to proceed as shown in Scheme B.

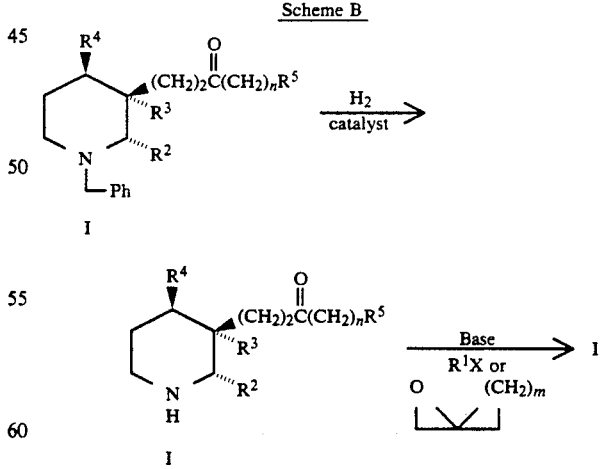

A suitably substituted compound of Formula I ($R^1$=benzyl) prepared as described above is dissolved in a solvent mixture comprising an acid, preferably hydrochloric acid, and an alcoholic solvent, preferably ethanol, and is treated with hydrogen gas at a pressure in the range of about 30 psi to about 50 psi in the presence of a catalyst, preferably palladium on Carbon, to afford a compound of Formula I wherein $R^1$ is hydrogen. This derivative can then be treated with an excess of an alkylating agent, e.g. $R^1X$ or

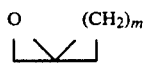

wherein X is bromine, chlorine or iodine, and m is an integer from 1 to 5, in the presence of an excess of a base, such as sodium bicarbonate, in a solvent, such as acetonitrile, to afford compounds of Formula I wherein $R^1$ is other than benzyl.

The lower-alkyl 6-acyl-2-azabicyclo[2.2.2]octane-6-carboxylates of Formula II, required for the synthesis of the compounds of Formula I, are prepared as shown in Scheme C.

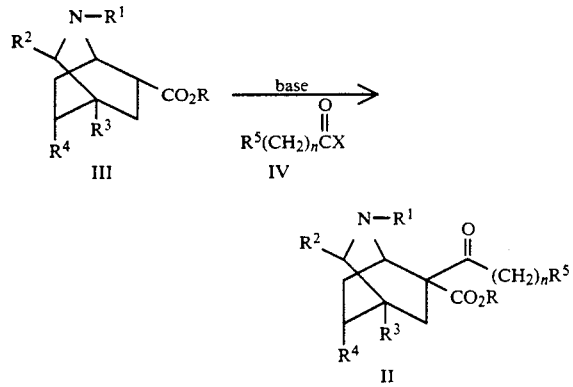

A suitably substituted lower-alkyl 2-azabicyclo[2.2.-2]octane-6-carboxylate of Formula III is treated with an excess of a base, preferably lithium diisopropylamide, followed by treatment with an excess of an appropriate acylating agent of Formula IV, e.g. an acid halide or haloformate, preferably an acid chloride or chloroformate, in a solvent, such as tetrahydrofuran, at a temperature in the range of from about $-78°$ C. up to about $25°$ C.

The lower-alkyl 2-azabicyclo[2.2.2]octane-6-carboxylates of Formula III required for the synthesis of the compounds of Formula II are prepared as shown in Scheme D.

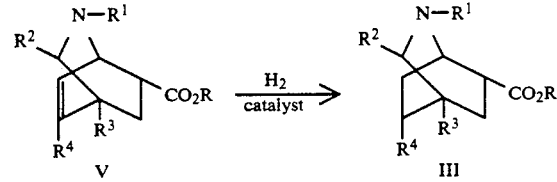

A suitably substituted lower-alkyl 2-azabicyclo[2.2.-2]oct-7-ene-6-carboxylate of Formula V or acid-addition salt thereof, e.g. the hydrochloride, is hydrogenated at a hydrogen pressure of from about 15 psi to about 50 psi, in the presence of a catalyst, preferably palladium on carbon, in an alcoholic solvent, such as ethanol. In those instances wherein $R^1$ is benzyl, debenzylation also occurs under these hydrogenation reaction conditions to produce a compound of Formula III wherein $R^1$ is hydrogen. An appropriate $R^1$ substituent can be reintroduced into the compounds of Formula III by treating the compound of Formula III or acid-addition salt thereof, e.g. the hydrochloride, wherein $R^1$ is hydrogen (a) with an excess of formaldehyde and an excess of a base, preferably triethylamine, in an alcoholic solvent, such as ethanol, in the presence of hydrogen gas at a hydrogen pressure in the range from about 15 psi up to about 50 psi to produce a compound of Formula III wherein $R^1$ is methyl; or (b) with an appropriate alkylating agent, e.g. $R^1X$ wherein $R^1$ is benzyl or lower-alkyl, in the presence of an excess of a base, such as potassium carbonate, in a solvent, such as acetonitrile, at a temperature in the range of from about $25°$ C. up to the boiling point of the solvent used.

The lower-alkyl 2-azabicyclo[2.2.2]oct-7-ene-6-carboxylates of Formula V can be prepared as shown in Scheme E.

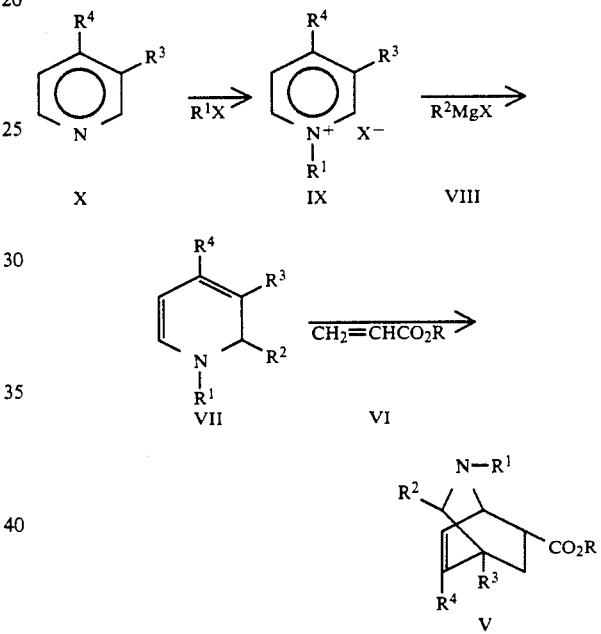

A suitably substituted pyridine derivative (X) is treated with an appropriate alkylating agent, $R^1X$ wherein $R^1$ is benzyl or lower-alkyl, in an alcoholic solvent, such as isopropanol, at a temperature in the range of from about $25°$ C. up to the boiling point of the solvent used, to afford a pyridinium salt of the Formula IX. The pyridinium salt (IX) is treated with an excess of an appropriate Grignard reagent (VIII), in a solvent, such as ether, at a temperature in the range of from about $0°$ C. up to about $35°$ C. to afford an appropriately substituted 1,2-dihydropyridine (VII). The 1,2-dihydropyridine (VII) is then treated with a suitable lower-alkyl acrylate (VI), in a solvent, such as toluene, at a temperature up to the boiling point of the solvent used to afford the lower-alkyl 2-azabicyclo[2.2.2]oct-7-ene-6-carboxylates of Formula V.

The appropriately substituted alkylating agent, $R^1X$ or

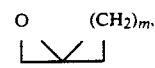

the acid halide or haloformate (IV), pyridine (X), Grignard reagent (VIII) and lower-alkyl acrylate (VI) are either commercially available or can be prepared by procedures well known in the art.

Simple chemical transformation which are conventional and well known to those skilled in the art of chemistry can be used for effecting changes in functional groups in the compounds of the invention. For example, hydrolysis of esters to produce the corresponding carboxylic acid, and dealkylation of ethers to produce the corresponding alcohols.

The compounds of Formula I are useful both in the free base form and in the form of acid-addition salts, and, both forms are within the purview of the invention. The acid-addition salts are often a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not vitiated by side effects ascribable to the anions. In practicing the present invention it is convenient to use the free base form or the hydrochloride, fumarate, toluenesulfonate, methanesulfonate or maleate salts. However, other appropriate pharmaceutically acceptable salts within the scope of the invention are those derived from other mineral acids and organic acids. The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by ion exchange procedures.

The structures of the compounds of the invention were established by the mode of synthesis, by elemental analysis, and by infrared, ultraviolet, nuclear magnetic resonance and mass spectroscopy. The course of the reactions and the identity and homogeneity of the products were assessed by thin layer chromatography (TLC) or gas-liquid chromatography (GLC).

The following examples will further illustrate the invention without, however, limiting it thereto. The abbreviation THF stands for tetrahydrofuran, HCl stands for hydrochloric acid and $CH_2Cl_2$ stands for dichloromethane.

PREPARATION OF STARTING MATERIALS

Preparation 1

(a)

A mixture of 3,4-lutidine (112 mL, 1.0 mole), benzyl chloride (115 mL, 1.0 mole) and isopropanol (500 mL) was refluxed under nitrogen for 5 hours and then was stirred at room temperature for 60 hours. The mixture was diluted with ether and the resulting white precipitate was filtered and dried to afford 178.3 g (76%) of N-(phenylmethyl)-3,4-dimethylpyridinium chloride.

(b)

A solution of methyl iodide (112 mL, 1.8 mole) in ether (225 mL) was added dropwise to a suspension of magnesium turnings (44 g, 1.8 mole) in ether (225 mL) under nitrogen over a period of 1 hour. The mixture was stirred at room temperature for 1 hour, transferred into a 1000 mL addition funnel and then was added to a suspension of N-(phenylmethyl)-3,4-dimethylpyridinium chloride (350 7 g, 1.5 mole) in ether (1500 mL) under a nitrogen atmosphere. The reaction mixture was stirred at room temperature for 24 hours and was then poured into a solution of saturated ammonium chloride (3 L). The organic layer was separated and the aqueous layer was extracted with ether (1000 mL). The combined ether layers were washed with water (500 mL), then brine (500 mL) and were dried over sodium sulfate and potassium carbonate. The solvent was removed in vacuo to afford 284.1 g (76%) of 1,2-dihydro-N-(phenylmethyl)-3,4-trimethylpyridine as an amber oil.

(c)

A solution of 1,2-dihydro-N-(phenylmethyl)-2,3,4-trimethylpyridine (284.1 g, 1.14 mole) in toluene (3000 mL) under nitrogen was treated with ethyl acrylate (162 mL, 1.5 mole). The mixture was refluxed for 21 hours and the solvent was removed in vacuo. The residue was dissolved in ethanol (300 mL), treated with 10N ethanolic.HCl and diluted with ether. A precipitate formed, which was collected by filtration and recrystallized from ethanol (150 mL)/ether (1400 mL) to afford 117.5 g (22%) of ethyl 3,4,8-trimethyl-2-(phenylmethyl)-2-azabicyclo[2.2.2]-oct-7-ene-6-carboxylate hydrochloride as a white powder, m.p. 184°–186° C. The mother liquor from the above recrystallization was treated with concentrated ammonium hydroxide (30 mL) and water (500 mL). The organic layer was separated, washed with brine and dried over potassium carbonate. The solvent was removed in vacuo and the residue was purified by column chromatography on silica eluting with ethyl acetate/hexane (25/75). The residue was dissolved in ethanol (50 mL), treated with 10.5N ethanolic HCl (10 mL) and diluted with ether (1200 mL). The product was collected by filtration and recrystallized from ethanol/ether to afford an additional 131.2 g of the product for a total yield of 47%.

(d)

A mixture of ethyl 3,4,8-trimethyl-2-(phenylmethyl)-2-azabicyclo[2.2.2]-oct-7-ene-6-carboxylate hydrochloride (17.4 g, 49.7 mol), 10% palladium on carbon (1.7 g) and ethanol (200 mL) was hydrogenated on a Parr hydrogenator at 50 psi for 6 hours. The mixture was removed from the Parr hydrogenator, cooled to 0° C. and triethylamine (7.0 mL, 50 mmol), followed by 37% formaldehyde (4.1 mL, 55 mmol) were added. The mixture was then placed back on the Parr hydrogenator at 50 psi for 1 hour. The reaction mixture was removed from the Parr hydrogenator, the catalyst was removed by filtration and the solvent was removed in vacuo. The residue was dissolved in water, basified with concentrated ammonium hydroxide (20 mL) and extracted with ether (3×300 mL). The combined organic layers were washed with brine (50 mL), dried over potassium carbonate and concentrated in vacuo to afford 11.5 g (96%) of ethyl 2,3,4,8-tetramethyl-2-azabicyclo[2.2.2]octane-6-carboxylate as a pale yellow oil.

(e)

To a solution of diisopropylamine (3.0 mL, 22 mmol) in THF (34 mL) at 0° C. under nitrogen was added n-BuLi (8.8 mL, 22 mmol, 2.5M in hexanes). A solution of ethyl 2,3,4,8-tetramethyl-2-azabicyclo[2.2.2]octane-6-carboxylate (4.8 g, 20 mmol) in THF (46 mL) was added to the mixture and the reaction was stirred at 0° C. for 1 hour. Ethyl chloroformate (2.3 mL, 24 mmol) in THF (3 mL) was then added and the mixture was stirred for 15 minutes. The reaction mixture was diluted with saturated ammonium chloride and partitioned between water and ether. The aqueous layer was extracted with ether (2X) and the combined organic layers were dried over anhydrous $MgSO_4$. The solvent was removed in vacuo and the residue was purified by column chromatography on silica gel eluting with ether/hexane (15/85) to afford 3.9 g (63%) of diethyl 2,3,4,8-tetramethyl-2-azabicyclo[2.2.2]octane-6,6-dicarboxylate as a yellow oil.

Preparation 2

(a)

A mixture of ethyl 3,4,8-trimethyl-2-(phenylmethyl)-2-azabicyclo[2.2.2]oct-7-ene-6-carboxylate hydrochloride (26.2 g, mmol), 10% palladium on carbon (2.6 g) and ethanol (200 mL) were placed on a Parr hydrogenator at 50 psi for 3.5 hours. The catalyst was removed by filtration and the solvent was removed in vacuo to afford crude ethyl 3,4,8-trimethyl-2-azabicyclo[2.2.2]octane-6-carboxylate hydrochloride as a yellow oil, which was used directly in the next step.

(b)

A mixture of the above crude product (approximately 75 mmol), potassium carbonate (104 g, 0.75 mol), benzyl chloride (8.6 mL, 75 mmol) and acetonitrile (500 mL) were refluxed under nitrogen for 24 hours. The reaction mixture was filtered and the solvent was removed in vacuo to afford 22.4 g (93%) of ethyl 3,4,8-trimethyl-2-(phenylmethyl)-2-azabicyclo[2.2.2]octane-6-carboxylate as a golden oil.

(c)

To a solution of diisopropylamine (13.2 mL, 94 mmol) in THF (175 mL) at −60° C. under nitrogen was added n-BuLi (36.2 mL, mmol, 2.6M hexane). The mixture was stirred for 30 minutes, cooled to −78° C. and ethyl 3,4,8-trimethyl-2-(phenylmethyl)-2azabicyclo[2.2.2]octane-6-carboxylate (26.8 g, 85 mmol) in THF (225 mL) was added. The mixture was stirred for 3 hours, then ethyl chloroformate (8.96 mL, 94 mmol) in THF (20 mL) was added dropwise. The mixture was stirred for 24 hours, quenched with saturated $NH_4Cl$, and poured into water (1000 mL). The solution was extracted with ether (3X), and the organic layers were combined and dried over $MgSO_4$. The ether layer was treated with charcoal and the solvent was removed in vacuo to afford 32.1 g (97%) of diethyl 3,4,8-trimethyl-2-(phenylmethyl)-2-azabicyclo[2.2.2]octane-6,6-dicarboxylate as a golden oil.

Preparation 3

To a solution of diisopropylamine (7.4 mL, 53 mmol) in THF (75 mL) at 0° C. under nitrogen was added n-BuLi (22 mL, 53 mmol). The mixture was stirred for 20 minutes, cooled to −70° C. and ethyl 2,3,4,8-tetramethyl-2-azabicyclo[2.2.2]octane-6-carboxylate (11.5 g, 48 mmol) in THF (75 mL) was added dropwise over 20 minutes. The mixture was stirred at −70° C. for 10 minutes, then 3-cyclopentylpropionyl chloride (8.1 mL, 53 mmol) in THF (75 mL) was added. The mixture was allowed to warm to 0° C. over a period of 30 minutes and was poured into saturated $NaHCO_3$ (300 mL). The solution was extracted with ether (3×300 mL), the ether extracts were combined and washed with water (50 mL), then brine (50 mL). The organic layer was dried over $K_2CO_3$ and concentrated in vacuo. The residue was dissolved in $CH_2Cl_2$ (500 mL), washed with 1.5N HCl (3×100 mL) and the aqueous layers were backwashed with $CH_2Cl_2$ (100 mL). The $CH_2Cl_2$ portions were washed with 5% $Na_2CO_3$ (50 mL), then water (50 mL) and the organic layer was concentrated in vacuo to afford the crude product as an oil. The product was purified by column chromatography on silica eluting with 10% ethyl acetate/hexane to 30% ethyl acetate/hexane/1% isopropylamine to afford 8.8 g (50%) of ethyl 2,3,4,8-tetramethyl-2-azabicyclo[2.2.2]octane-6-(3-cyclopentylpropionyl)-6-carboxylate.

Preparation 4

To a solution of diisopropylamine (13.4 mL, 95.2 mmol) in THF (95 mL) at −78° C. under nitrogen was added n-BuLi (38.1 mL, 95 mmol) at a rate of 0.7 mL/minute. The mixture was stirred for 5 minutes, then ethyl 2,3,4,8-tetramethyl-2-azabicyclo[2.2.2]octane-6-carboxylate (19.0 g, 79.4 mmol) in THF (50 mL) was added dropwise over 30 minutes. The reaction mixture was stirred at −78° C. for 3 hours, then a solution of 2-furoyl chloride (9.4 mL, 95 mmol) in THF (50 mL) was added. The mixture was stirred for 24 hours, quenched with saturated $NH_4Cl$ (50 mL) and poured into water (1 L). The solution was extracted with ether (3×100 mL), the organic layers were combined and dried over $MgSO_4$. The solvent was removed in vacuo and the residue was filtered through florisil eluting with ether/hexane (1/1) to afford 18.5 g (70%) of ethyl 2,3,4,8-tetramethyl-2-azabicyclo[2.2.2]octane-6-(2-furoyl)-6-carboxylate.

Preparation 5

To a solution of diisopropylamine (7.7 mL, 55 mmol) in THF (75 mL) at 0° C. under nitrogen was added n-BuLi (24 mL, 55 mmol). The mixture was stirred for 25 minutes, cooled to −78° C. and ethyl 3,4,8-trimethyl-2-(phenylmethyl)-2-azabicyclo[2.2.2]octane-6-carboxylate (15.7 g, 50 mmol) in THF (100 mL) was added dropwise. The mixture was stirred at −78° C. for 30 minutes, then 3-cyclopentylpropionyl chloride (8.4 mL, 55 mmol) in THF (40 mL) was added. The reaction mixture was warmed to room temperature over 24 hours, poured into saturated $NH_4Cl$ (250 mL) and extracted with ether (3×200 mL). The combined organic layers were washed with water (50 mL), saturated $NaHCO_3$ (2×50 mL), then brine (50 mL) and were dried over $Na_2SO_4$. The solvent was removed in vacuo and the residue was purified by column chromatography on silica gel eluting with hexane (100%) to hexane/ethyl acetate (98/2) to afford 13.1 g (60%) of ethyl 2,3,4,8-trimethyl-2-(phenylmethyl)-2-azabicyclo[2.2.-2]octane-6-(3-cyclopenylpropionyl)-6-carboxylate.

Preparation 6

Following a procedure similar to that described in Preparation 4 but substituting 3-furoyl chloride for 2-furoyl chloride there was obtained 13.7 g (62%) of ethyl 2,3,4,8-tetramethyl-2-azabicyclo[2.2.2]octane-6-(3-furoyl)-6-carboxylate as a brown oil.

Preparation 7

Following a procedure similar to that described in Preparation 4 but substituting the appropriate acid chloride, $ClC(O)(CH_2)_nR^5$, for 2-furoyl chloride it is contemplated that the compounds listed in Table 1 can be prepared.

TABLE 1

| Preparation | n | $R^5$ |
|---|---|---|
| 7a | 3 | (thiophene) |
| 7b | 0 | (oxazole) |
| 7c | 1 | $OCH_3$ |
| 7d | 0 | $CH_3CH_2$ |
| 7e | 0 | (phenyl) |

Preparation 8

By a process similar to that described in Preparations 1a-e it is contemplated that diethyl 8-ethyl-2,3,4-trimethyl-2-azabicyclo[2.2.2]octane-6,6-dicarboxylate and diethyl 3,8-diethyl-2,4-dimethyl-2-azabicyclo[2.2.-2]octane-6,6-dicarboxylate can be prepared from 4-ethyl-3-methylpyridine and the appropriate Grignard reagent.

Preparation 9

Following procedures similar to those described in preparations 1a-e there was obtained:

358.4 g (82%) of N-benzyl-4-methylpyridinium chloride from 4-picoline (195 mL, 2 mol), benzyl chloride (230 mL, 2 mol) and isopropanol (1000 mL). The product was recrystallized from isopropanol (800 mL)/ether (1400 mL) to afford cream colored crystals.

(b)

1,2-Dihydro-N-benzyl-2,4-dimethylpyridine from N-benzyl-4-methylpyridinium chloride (330 g, 1.5 mmol), methyl iodide (112 mL, 1.8 mmol), magnesium turnings (44 g, 1.8 mmol), and ether (total of 2250 mL), which was used without purification directly in Preparation 9c.

(c)

214.1 g (42%) of ethyl 3,8-dimethyl-2-(phenylmethyl)-2-azabicyclo[[2.2.2]-oct-7-ene-6-carboxylate hydrochloride as cream colored crystals from 1,2-dihydro-N-benzyl-2,4-dimethylpyridine (298.7 g, 1.5 mol), ethyl acrylate (162 mL, 1.5 mol) and toluene (2 L). The product was recrystallized from ethanol/acetonitrile/ether and had a melting point of 223°-225° C.

(d)

43.5 g (96%) of ethyl 2,3,8-trimethyl-2-azabicyclo[2.2.2]octane-6-carboxylate as a pale yellow oil from ethyl 3,8-dimethyl-2-(phenylmethyl)-2-azabicyclo[2.2.2]-oct-7-ene-6-carboxylate hydrochloride (67.2 g, 200 mmol), 10% palladium on carbon (3.6 g), ethanol (200 mL), methanol (200 mL), and water (40 mL) for step 1, and triethylamine (28 mL), and 37% aqueous formaldehyde (16.6 mL, 222.6 mmol) for step 2. The product was purified by a Kugelrohr distillation at 0.2 mm Hg and 65°-80° C.

(e)

54.2 g (94%) of diethyl 2,3,8-trimethyl-2-azabicyclo[2.2.2]octane-6,6-dicarboxylate as a pale yellow oil from ethyl 2,3,8-trimethyl-2-azabicyclo[2.2.2]octane-6-carboxylate (43.5 g, 193 mmol), diisopropylamine (30 mL, 213 mmol), n-BuLi (85 mL, 212.3 mmol, 2.5M hexanes) and THF (700 mL). The product was purified by column chromatography on silica eluting with hexanes/ethyl acetate (4/1).

Preparation 10

Following a procedure similar to that described in Preparation 1, parts a, b, and c there was obtained:

(a)

N-(Phenylmethyl)-5,6,7,8-tetrahydroisoquinolinium bromide (97.6 g, 95%) as pale creamed colored crystals from 5,6,7,8-tetrahydroisoquinoline (45 g, 338 mmol), benzyl bromide (57.8 g, 38 mmol) and isopropanol (450 ml).

(b)

N-(Phenylmethyl)-1-methyl-1,2,5,6,7,8-hexahydroisquinoquinoline (66.5 g, 84%) as a golden oil from N-phenylmethyl-5,6,7,8-tetrahydroisoquinolinium bromide (100.6 g, 330 mmol), magnesium turnings (9.7 g, 0.4 mol), methyl iodide (56.8 g, 0.4 mol) and ether (650 mL). The product was used directly in the next step without purification.

(c)

Ethyl 2,3,5,6,7,8-hexahydro-1-methyl-2-(phenylmethyl)-1H-3,8a-ethanoisoouinoline-10-carboxylate hydrochloride (40.0 g, 2%) as a white solid, m.p. 149°-151° C. when recrystallized from ethanol/ether, from N-phenylmethyl-1-methyl-1,2,5,6,7,8-hexahydroisoquinoline (66.5 g, 0.28 mol), toluene (600 mL) and ethyl acrylate (40 mL, 0.4 mol).

Following a procedure similar to that described in Preparation 2, parts a and b there was obtained:

(d)

Ethyl 2,3,4,4a,5,6,7,8-octahydro-1-methyl-1H-3.8a-ethanoisoquinoline-10-carboxylate hydrochloride from ethyl-2,3,5,6,7,8-hexahydro-1-methyl-2-(phenylmethyl)-1H-3,8a-ethanoisoquinoline-10-carboxylate hydrochloride (26.4 g, 70 mmol), ethanol (200 mL) and 10% palladium on carbon (1.0 g). The product was used directly in the next step without purification.

(e)

Ethyl 2,3,4,4a,5,6,7,8-octahydro-1-methyl-2-(phenylmethyl)-1H-3,8a-ethanoisoquinoline-10-carboxylate as a yellow oil, from ethyl 2,3,4,4a,5,6,7,8-octahydro-1-methyl-1H-3,8a-ethanoisoquinoline-10-carboxylate hydrochloride of Preparation 10d, acetonitrile (500 mL), benzyl bromide (8.1 mL, 70 mmol) and potassium carbonate (97 g, 700 mmol).

(f)

To a solution of diisopropylamine (17.4 mL, 124 mmol) in THF (200 mL) at 0° C. was added n-BuLi (47.5 mL, 124 mmol). The mixture was cooled to −78° C. and ethyl 2,3,4,4a,5,6,7,8-octahydro-1-methyl-2-(phenylmethyl)-1H-3,8a-ethanoisoquinoline-10-carboxylate (35.4 g, 103 mmol) in THF (200 mL) was added dropwise over 75 minutes. The mixture was stirred at −78° C. for 20 minutes, then 3-cyclopentylpropionyl chloride (19.1 mL, 124 mmol) was added via syringe. The mixture was slowly warmed to room temperature and was stirred for 24 hours. The reaction mixture was poured into saturated $NH_4Cl$, and the aqueous layer was separated and extracted with ether (2×400 mL). The combined organic layers were washed with saturated sodium chloride (2×50 mL), dried over $Na_2SO_4$ and concentrated in vacuo. The oily residue was dissolved in hexane (1000 mL) and extracted with 0.1N aqueous HCl (5×100 mL). The HCl extracts were combined, back washed with hexane (200 mL), neutralized with concentrated $NH_4OH$ and extracted with ether (3×100 mL). The ether extracts were washed with saturated sodium chloride, dried over $Na_2SO_4$ and concentrated in vacuo to afford 9.4 g of recovered starting material. The hexane layers were combined, washed with saturated $NaHCO_3$ then saturated sodium chloride and were dried over $Na_2SO_4$, and concentrated in vacuo to afford 41.6 g of ethyl 10-(3-cyclopentylpropionyl)-2,3,4,4a,5,6,7,8-octahydro-1-methyl-2-(phenylmethyl)-1H-3,8a-ethanoisoquinolinyl-10-carboxylate as a pale yellow oil.

Preparation of Final Products

Example 1

To diethyl 2,3,4,8-tetramethyl-2-azabicyclo[2.2.2]octane-6,6-dicarboxylate (121 g, 389 mmol) at 0° C. was added formic acid (121 mL, 3.2 mol), followed by triethylamine (179 mL, 1.3 mol). The mixture was slowly heated to 160° C. over a period of 2 hours and was stirred at 160° C. for 20 minutes. The mixture was cooled to room temperature, and allowed to stand under nitrogen for 24 hours. The mixture was basified by the addition of saturated $NaHCO_3$ and was extracted with ether (3X). The organic layers were combined, washed with saturated $NaHCO_3$ then brine and were dried over anhydrous $MgSO_4$. The solvent was removed in vacuo and the residue was taken up in 0.5N HCl (500 mL) and washed with hexane (3X). The aqueous layer was basified with concentrated $NH_4OH$ and extracted with ether (3X). The ether layer was dried over $MgSO_4$ and concentrated in vacuo to afford 34 g (36%) of ethyl 3-(1,2,3,4-tetramethyl-3-piperidine)-propanoate as a yellow oil. The combined aqueous phases were concentrated in vacuo and the residue was triturated with hot ethanol (800 mL at 70° C.). The solution was filtered, triturated with additional hot ethanol (300 mL) and filtered once again. The ethanol filtrates were combined, acidified with concentrated $H_2SO_4$ and refluxed for 24 hours under nitrogen. The solution was basified with concentrated $NH_4OH$ and extracted with ether (3X). The ether layers were combined, washed with saturated $NaHCO_3$ (2X) and dried over $MgSO_4$. The solvent was removed in vacuo to afford 28.5 g of additional product for a total yield of 62.5 g (67%). The product was treated with p-toluenesulfonic acid to afford ethyl-3-[1,2,3,4-tetramethyl-3-piperidine]propanoate p-toluenesulfonate as a white powder, m.p. 171°–171.5° C.

Example 2

A mixture of ethyl 2,3,4,8-tetramethyl-2-azabicyclo[2.2.2]octane-6-(3-cyclopentylpropionyl)-6-carboxylate (8.5 g, 23 mmol), formic acid (14 mL, 371 mmol) and mesitylene (375 mL) was refluxed under nitrogen for 20 hours. The reaction mixture was cooled to room temperature, washed with 10% NaOH (3×100 mL), water (2×50 mL) and brine (100 mL). The aqueous layers were combined and extracted with ether (2×300 mL). The organic layers were combined, dried over $Na_2SO_4$ and concentrated in vacuo. The residue was purified by column chromatography on silica eluting with hexane (100%) to 1% isopropylamine/15% ethyl acetate/hexane to afford 3.3 g (64%) of 1-cyclopentyl-5-(1,2,3,4-tetramethyl-3-piperidinyl)-3-pentanone. The free base was dissolved in ethanol (5 mL), treated with ethanolic HCl (15 mL) and diluted with ether (20 mL). The solvents were removed in vacuo and the oily residue was crystallized from ether (50 mL)/acetonitrile (2 mL). The salt was collected by filtration and recrystallized from acetonitrile (5 mL)/ether (50 mL) to afford 2.9 g of 1-cyclopentyl-5-(1,2,3,4-tetramethyl-3-piperidinyl)-3-pentanone hydrochloride as a white solid, m.p. 155°–157° C.

Example 3

(a)

To a mixture of ethyl 3,4,8-trimethyl-2-(phenylmethyl)-2-azabicyclo[2.2.2]octane-6-(3-cyclopentylpropionyl)-6-carboxylate (13.0 g, 30 mmol) and formic acid (11 mL, 0.3 mol) at 0° C. was added dropwise triethylamine (16.7 mL, 0.12 mol). The mixture was heated to 160° C. for 2 hours, cooled to room temperature and diluted with cold water (100 mL). The solution was neutralized with concentrated $NH_4OH$ (20 mL) and extracted with ether (3×100 mL). The organic layers were combined, washed with brine (50 mL), dried over $Na_2SO_4$ and the solvent was concentrated in vacuo. The residue, which contained the desired product as well as recovered starting material, was treated with formic acid (12 mL) and triethylamine (18 mL) and was heated at 160° C. for 40 hours. The mixture was dissolved in water (100 mL), neutralized with concentrated $NH_4OH$ (30 mL) and extracted with ether (3×100 mL). The combined ether extracts were washed with saturated sodium chloride, dried over $Na_2SO_4$ and concentrated in vacuo. The residue was purified by column chromatography on silica gel eluting with hexane (100%) to 1% triethylamine/10% ethyl acetate/hexane to afford 6.6 g (59.5%) of 1-cyclopentyl-5-2,3,4-trimethyl-1-(phenylmethyl)-3-piperidinyl-3-pentanone.

(b)

A mixture of 1-cyclopentyl-5-[2,3,4-trimethyl-1-(phenylmethyl)-3-piperidinyl]-3-pentanone (6.3 g, 17 mmol), 5 ethanolic HCl (4 mL, 20 mmol) and 10% palladium on carbon (1.2 g) was placed on a Parr hydrogenator at 50 psi for 3 hours, then palladium (II) chloride (0.6 g) and charcoal (1.0 g) were added and the mixture was hydrogenated at 50 psi for 2.5 hours. The catalysts were removed by filtration and the solvent was removed in vacuo. The residue was partitioned between 10% $Na_2CO_3$ (100 mL) and ether (2 × 150 mL), the organic layers were separated and washed with brine (50 mL). The organic layers were dried over $Na_2SO_4$ and the solvent was removed in vacuo to afford 4.0 g (84%) of 1-cyclopentyl-5-(2,3,4-trimethyl-3-piperidinyl)-3-pentanone. 2.1 g of the product was used directly in the next step, while the remaining 1.9 g was purified by column chromatography on silica gel eluting with 1–10% triethylamine/ether to afford 1.1 g of the purified product. Treatment of the purified product with 5N ethereal HCl followed by dilution with ether and recrystallization of the solid thus obtained from ethanol/ether afforded 0.8 g of 1-cyclopentyl-5-(2,3,4-trimethyl-3-piperidinyl)-3-pentanone hydrochloride as a white powder, m.p. 127°–128° C.

(c)

A mixture of 1-cyclopentyl-5-(2,3,4-trimethyl-3-piperidinyl)-3-pentanone (2.1 g, 7.5 mmol), acetonitrile (25 mL), sodium bicarbonate (2.2 g, 26 mmol) and oxaspiropentane (0.74 g, 9 mmol, 30% in $CH_2Cl_2$) was stirred at room temperature for 3.5 hours. The mixture was diluted with ether, filtered, and the solvent was removed in vacuo. The residue was purified by column chromatography on silica gel eluting with 4% triethylamine/5% ether/ hexanes to afford 1.9 g (73% of 1-cyclopentyl-5-[1-[(1-hydroxycyclopropyl)methyl]-2,3,4-trimethyl-3-piperidinyl]-3-pentanone. The product was dissolved in ethanol, treated with 5.3N ethereal HCl and diluted with ether. The solid thus obtained was recrystallized from ethanol/ether to afford 1.7 g of the hydrochloride salt as a white solid, m.p. 135°–137° C.

Example 4

Following a procedure similar to that described in Example 3a, 5.0 g (49%) of 1-(3-furanyl)-3-(1.2.3.4-tetramethyl-3-piperidinyl)-1-propanone was obtained, after purification by column chromatography on silica gel eluting with 0.5% isopropylamine/25% ether/hexane, from ethyl 2,3,4,8-tetramethyl-2-azabicyclo[2.2.2]octane-6-(3-furoyl)-6-carboxylate of preparation 6 (13.0 g, 39.0 mmol) and formic acid/triethylamine (130 mL, 2/3 v/v). The product was dissolved in acetonitrile/ether (1/1), treated with methanesulfonic acid and diluted with ether to afford 5.2 g of the methanesulfonate salt as a tan solid, m.p. 144°–146° C.

Example 5

Following a procedure similar to that described in Example 3a, 3.9 g (27%) of 1-(2-furanyl)-3-(1,2,3,4-tetramethyl-3-piperidinyl)-1-propanone was obtained, after purification by column chromatography on silica gel eluting with 0.5% isopropylamine/25% ether/hexane, from ethyl 2,3,4,8-tetramethyl-2-azabicyclo[2.2.2]octane-6-(2-furoyl)-6-carboxylate of preparation 4 (18.45 g, 55.3 mmol) and formic acid/triethylamine (185 mL, 2/3 v/v). The product was treated with ethanolic HCl and the resulting solid was recrystallized from isopropanol to afford 2.5 g of the hydrochloride salt as a white solid, m.p. 194° C. (dec.).

Example 6

Following a procedure similar to that described in Example 3a, 10.0 g (98%) of ethyl 3-[2,3,4-trimethyl-1-(phenylmethyl)-3-piperidine)propanoate was obtained from diethyl 3,4,8-trimethyl-2-(phenylmethyl)-2-azabicyclo[2.2.2]octane-6,6-dicarboxylate of preparation 2C (12.5 g, 32.0 mmol), formic acid (11.0 mL) and triethylamine (14.7 mL). The product was treated with ethanolic HCl, and the resulting solid was recrystallized from ethanol/ether to afford 5.1 g of the hydrochloride salt as a white powder, m.p. 130.5°–132.5° C.

Example 7

Following a procedure similar to that described in Example 3a but substituting the appropriate compound of Formula II for ethyl 3,4,8-trimethyl-2-(phenylmethyl)-2-azabicyclo[2.2.2]octane-6-(3-cyclopentylpropionyl)-6-carboxylate it is contemplated that the compounds of Formula I listed in Table 2 can be prepared.

TABLE 2

| Example | $R^1$ | $R^2$ | $R^3$ | $R^4$ | $R^5$ | n |
|---------|-------|-------|-------|-------|-------|---|
| 7a | $CH_3$ | Et | $CH_3$ | Et | OEt | 0 |
| 7b | $CH_3$ | $CH_3$ | $CH_3$ | Et | OEt | 0 |
| 7c | $CH_3$ | $CH_3$ | $CH_3$ | $CH_3$ | 2-thienyl | 3 |
| 7d | $CH_3$ | $CH_3$ | $CH_3$ | $CH_3$ | isoxazolyl | 0 |
| 7e | $CH_3$ | $CH_3$ | $CH_3$ | $CH_3$ | $OCH_3$ | 1 |
| 7f | $CH_3$ | $CH_3$ | $CH_3$ | $CH_3$ | $CH_2CH_3$ | 0 |
| 7g | $CH_3$ | $CH_3$ | $CH_3$ | $CH_3$ | phenyl | 0 |

Example 8

Following a procedure similar to that described in Example 3C but substituting cyclopropylmethyl bromide for oxaspiropentane it is contemplated that 1-cyclopentyl-5-[1-[(1-cyclopropyl)methyl]-2,3,4-trimethyl-3-piperidinyl]-3-pentanone can be prepared.

Example 9

A mixture of diethyl 2,3,8-trimethyl-2-azabicyclo[2.2.2]octane-6-dicarboxylate (54.2 g, 182 mol), formic acid (140 mL) and triethylamine (210 mL) were heated to 160° C. for 45 minutes. The reaction mixture was cooled, diluted with water (300 mL) and basified with ammonium hydroxide. The mixture was extracted with ether (3×300 mL), and the organic layer was dried over Na$_2$SO$_4$. Removal of the solvents in vacuo and analysis of the residue indicated that the reaction had not gone to completion. The residue was then resubjected to the above-mentioned reaction conditions for a time of four hours to afford 27.3 g (66%) of ethyl 3-(1,2,4-trimethyl-3-piperidine)propanoate. The aqueous layers were combined, concentrated to dryness and triturated with ethanol (2×500 mL). The mixture was filtered, concentrated to approximately 250 mL, filtered again and concentrated in vacuo to afford a yellow oil. The oil was dissolved in ethanol (500 mL) and treated with concentrated H$_2$SO$_4$ until a Ph=1.5 was obtained. The mixture was once again filtered to remove any precipitated salts, the salts were washed with ethanol (2×250 mL) and the resulting solution was refluxed for 6 hours. The solvent was concentrated in vacuo, the residue was dissolved in water (500 mL) and the mixture was neutralized with ammonium chloride. The mixture was extracted with ether (3×300 mL), and the ether extracts were combined, washed with brine (100 mL), dried over anhydrous MgSO$_4$ and concentrated in vacuo to afford an additional 8.4 g of product. The crude product was combined with an additional 7.6 g of crude product from a similar experimental run, and the mixture (16 g) was purified by a Kugelrohr distillation at 80°-95° C. and 0.4 mm Hg, followed by column chromatography on silica gel eluting with 0.5% isopropylamine/hexane to 2% isopropylamine/hexane to afford 12.2 g of purified product. The product was dissolved in ether, treated with 6.2N ethereal HCl and diluted with acetonitrile to afford 11.4 g of the hydrochloride salt, m.p. 88°-90° C.

Example 10

Following a procedure similar to that described in Example 3, parts a, b and c, there was obtained:

(a)

1-Cyclopentyl-5-octahydro-2-(phenylmethyl)-1-methyl-8a(1H)-isoquinolinyl]-3-pentanone (8.5 g), from ethyl 10-(3-cyclopentylpropionyl)-2,3,4,4a,5,6,7,8-octahydro-1-methyl-2-(phenylmethyl)-1H-3,8a-ethanoisoquinolinyl-10-carboxylate (40.5 g, 87 mmol), formic acid (40 mL, 1.06 mol) and triethylamine (60 mL, 430 mmol). The product was purified by column chromatography on silica gel eluting with hexane (100%) to 50% ethyl acetate/hexane.

(b)

1-Cyclopentyl-5-[octahydro-1-methyl-8a(1H)-isoquinomethyl]-3-pentanone (2.5 g), from 1-cyclopentyl-5-[octahydro-2-(phenylmethyl)-1-methyl-8a(1H)-isoquinolinyl]-3-pentanone (8.5 g, 21.4 mmol), 6.5 m ethereal HCl (3.3 mL, 21.4 mmol), ethanol (100 mL) and 10% palladium on carbon (0.9 g). The product was purified by column chromatography on silica gel eluting with hexane (100%) to 10% triethylamine/ether, followed by 20% triethylamine/20% ether/hexane, then 20% triethylamine/ether.

(c)

1-Cyclopentyl-5-octahydro-2-(1-hydroxycyclopropyl)methyl]-1-methyl-8a(1H)-isoquinolinyl]-3-pentanone (2.8 g, 97%), after purification by column chromatography on silica eluting with triethylamine/ether/hexane (5/5/90), from 1-cyclopentyl-5[octahydro-1-methyl-8a(1H)-isoquinolinyl]-3-pentanone (2.4 g, 7.8 mmol), oxospiropentane (2.3 g, 10 mmol, 30% in CH$_2$Cl$_2$), NaHCO$_3$ (2.9 g, 25 mmol) and acetonitrile (25 mL). The product was dissolved in isopropanol, treated with ethereal HCl and diluted with ether to afford an oil. The oil was dissolved in ethyl acetate and cooled to afford 1.7 g, of the hydrochloride salt, m.p. 124°-126° C.

Example 11

It is contemplated that refluxing ethyl 3-(1,2,3,4-tetramethyl-3-piperidine)propanoate with sodium hydroxide in ethanol, followed by acidification on an appropriate ion-exchange resin will afford 3-(1,2,3,4-tetramethyl-3-piperidine)propionic acid.

BIOLOGICAL TEST RESULTS

In standard biological test procedures, representative examples of the compounds of the invention have been found to bind with high affinity to sigma receptors, and are thus useful in the treatment of central nervous system disorders such as psychoses, dystonias, dyskinesias, Parkinson's syndrome, Huntington's chorea, Tourette syndrome and the like, especially psychoses, e.g. schizophrenic psychoses, manic depressive psychoses and the like.

The sigma receptor binding activity of representative compounds of the invention was demonstrated by following a procedure essentially as described by Hudkins and DeHaven-Hudkins, Life Sci. 1991, 49(17), 1229-1235.

Brain tissue was prepared from male Hartley guinea pigs (Hazelton Labs, Denver, Pa.) which were anesthetized with CO$_2$ and sacrificed by decapitation. All animal care and use procedures were in accord with the "Guide for the Care and Use of Laboratory Animals" (NIH Publ. No 86-23, 1985). Homogenization was performed in 10 volumes (wt/vol) of 0.32M sucrose with a Brinkmann Polytron at setting 5, 30 sec. The homogenate was centrifuged at 900 x g for 10 min at 4° C., and the supernatant was collected and centrifuged at 22,000 x g for 20 min at 4° C. The pellet was resuspended in 10 volumes of Tris-HCl buffer (50 mM, pH 7.4), incubated at 37° C. for 30 min, and centrifuged at 22,000 x g for 20 min at 4° C. Following this, the pellet was resuspended in Tris buffer and frozen in 5-10 mL aliquots corresponding to a tissue concentration of 100 mg/mL, at −70° C. Binding characteristics of the membranes were stable for at least one month when stored at −70° C.

On the day of the assay, membrane aliquots were thawed, resuspended in fresh Tris-HCl buffer and stored on ice until use. Each assay tube contained 100 μL of [3H]-(+)-pentazocine at a final concentration of approximately 0.5 nM, 100 μL of various concentrations of the compounds of interest, 500 μL of the tissue suspension and 300 μL of buffer to a final assay volume of 1 mL and a final tissue concentration of approximately 8 mg/tube, corresponding to approximately 0.15 mg protein/tube. Nonspecific binding was defined by addition of a final concentration of 1 μM haloperidol to blank tubes. All tubes were incubated at 37° C. for 150 min before termination of the reaction by rapid filtration over Whatman GF/B glass fiber filters that were presoaked in a solution of 0.5% polyethyleneimine for at least 1 hr prior to use. Filters were washed with three 4 ml volumes of cold Tris-HCl buffer.

Following addition of scintillation cocktail, samples were allowed to equilibrate for at least 4 hr. The amount of bound radioactivity was determined by liquid scintillation spectrometry using a Beckman LS 5000 TA liquid scintillation counter with an efficiency for tritium of approximately 60%. The results are reported as a percent (%) inhibition of binding at 10 μM.

Scatchard parameters and inhibition constants (Ki values) for the binding of test compounds were also calculated using the EBDA/LIGAND program (McPherson, J. Pharmacol. Meth. 1985, 14, 213–228), purchased from Elsevier/Biosoft, Inc. The Ki values are expressed as the mean ±SEM of at least three separate determinations performed in triplicate.

The following Table summarizes the results obtained from the testing of representative compounds of the invention.

TABLE 3

| Example No. | Percent Inhibition | $K_i$ (nM) |
|---|---|---|
| 1 | 70 | — |
| 2 | 100 | — |
| 3c | 98 | — |
| 3b | 96 | — |
| 4 | 78 | — |
| 5 | 57 | — |
| 6 | 99 | 39 ± 5 |
| 10 | 84 | — |

The compounds of the invention can be prepared for pharmaceutical use by conventional pharmaceutical procedures that are well known in the art; that is, by formulating a pharmaceutical composition which comprises compounds of the invention or their pharmaceutically acceptable salts together with one or more physiologically acceptable carriers, adjuvants, diluents or vehicles, for oral administration in solid or liquid form, parenteral administration, topical administration or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size component and the patient's response thereto. An effective dosage amount of the active component can thus readily be determined by the clinician after a consideration of all criteria and using his best judgment on the patient's behalf.

We claim:

1. A compound of the formula:

wherein:

$R^1$ is hydrogen, lower-alkyl, phenyl-lower-alkyl, $C_3$–$C_7$-monocyclic cycloalkyl-lower-alkyl, or hydroxy-$C_3$–$C_7$-monocycliccycloalkyl-lower-alkyl;

$R^2$ is lower-alkyl;

$R^3$ is hydrogen or lower-alkyl;

$R^4$ is lower-alkyl;

n is an integer from zero to three; and $R^5$ is hydroxy, lower-alkoxy, lower-alkyl, $C_3$–$C_7$-monocyclic cycloalkyl, phenyl, or a 5-membered aromatic monocyclic heterocycle selected from the group consisting of furanyl, thienyl and isoxazolyl; or a pharmaceutically acceptable acid-addition salt thereof; with the proviso that when n is zero, $R^5$ is other than hydroxy.

2. A compound according to claim 1 wherein $R^1$ is hydrogen, lower-alkyl, phenyl-lower-alkyl or hydroxy-$C_3$–$C_7$-monocyclic-cycloalkyl-lower-alkyl; $R^3$ is lower-alkyl; $R^4$ is lower-alkyl; and $R^5$ is lower-alkoxy, $C_3$–$C_7$-monocyclic cycloalkyl or a 5-membered aromatic monocyclic heterocyclic selected from the group consisting of furanyl and thienyl.

3. A compound according to claim 2 wherein $R^2$ is methyl; $R^3$ and $R^4$ are methyl; and n is zero or two.

4. A compound according to claim 3 wherein $R^1$ is hydrogen, methyl, benzyl or hydroxycyclopropylmethyl; and $R^5$ is lower-alkoxy, $C_3$–$C_7$-monocyclic cycloalkyl or furanyl.

5. A compound according to claim 4 wherein $R^5$ is ethoxy, cyclopentyl, or 2- or 3-furanyl.

6. Ethyl 3-[2,3,4-trimethyl-1-(phenylmethyl)-3-piperidine]propanoate or an acid-addition salt thereof according to claim 5.

7. A pharmaceutical composition which comprises an antipsychotically effective amount of compound of the formula

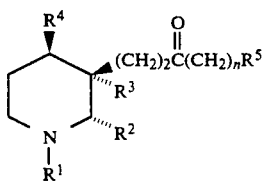

wherein:
R[1] is hydrogen, lower-alkyl, phenyl-lower-alkyl, $C_3$–$C_7$-monocyclic cycloalkyl-lower-alkyl, or hydroxyl-$C_3$–$C_7$-monocyclic-cycloalkyl-lower-alkyl;
R[2] is lower-alkyl;
R[3] is hydrogen or lower-alkyl;
R[4] is lower-alkyl;
n is an integer from zero to three; and
R[5] is hydroxy, lower-alkoxy, lower-alkyl, $C_3$–$C_7$-monocyclic cycloalkyl, phenyl, or a 5-membered aromatic monocyclic heterocycle selected from the group consisting of furanyl, thienyl and isoxazolyl; or a pharmaceutically acceptable acid-addition salt thereof, together with a pharmaceutically acceptable carrier, adjuvant, diluent or vehicle; with the proviso that when n is zero, R[5] is other than hydroxy.

8. A pharmaceutical composition according to claim 7 wherein R[1] is hydrogen, methyl, benzyl or hydroxycyclopropylmethyl; R[2] is methyl; R[3] and R[4] are methyl; n is zero or two; and R[5] is lower-alkoxy, $C_3$–$C_7$-monocyclic cycloalkyl, or furanyl.

9. A pharmaceutical composition according to claim 8 wherein the compound is ethyl 3-[2,3,4-trimethyl-1-(phenylmethyl)-3-piperidine]propanoate or an acid addition salt thereof.

10. A method for the treatment of psychosis which comprises administering to a patient in need of such treatment an effective amount of a compound of the formula

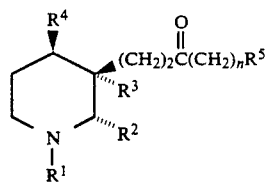

wherein:
R[1] is hydrogen, lower-alkyl, phenyl-lower-alkyl, $C_3$–$C_7$-monocyclic cycloalkyl-lower-alkyl, or hydroxy-$C_3$–$C_7$-monocyclic-cycloalkyl-lower-alkyl;
R[2] is lower-alkyl;
R[3] is hydrogen or lower-alkyl;
R[4] is lower-alkyl;
n is an integer from zero to three; and
R[5] is hydroxy, lower-alkoxy, lower-alkyl, $C_3$–$C_7$-monocyclic cycloalkyl, phenyl, or a 5-membered aromatic monocyclic heterocycle selected from the group consisting of furanyl, thienyl and isoxazolyl; or a pharmaceutically acceptable acid-addition salt thereof; with the proviso that when n is zero, R[5] is other than hydroxy.

11. A method according to claim 10 wherein R[1] is hydrogen, methyl, benzyl or hydroxycyclopropylmethyl; R[2] is methyl; R[3] and R[4] are methyl; n is zero or two; and R[5] is lower-alkoxy, $C_3$–$C_7$-monocyclic cycloalkyl or furanyl.

12. A method according to claim 11 wherein the compound is ethyl 3-[2,3,4-trimethyl-1-(phenylmethyl)-3-piperidine]propanoate.

* * * * *